US 6,875,422 B2

(12) United States Patent
Nonomura et al.

(10) Patent No.: US 6,875,422 B2
(45) Date of Patent: Apr. 5, 2005

(54) ORAL TREATMENT/CARE AGENT

(76) Inventors: Yuusuke Nonomura, 2-54, Nishisato-cho, Meito-ku, Nagoya-shi, Aichi 465-0084 (JP); Tonami Ikuta, 47-7, Miyanokawachi, Kawaura-machi, Amakusa-gun, Kumamoto 863-1212 (JP); Hideki Matsumoto, 10-4, Ochikawa, Takatsuki-cho, Ika-gun, Shiga 529-0232 (JP)

( * ) Notice: Subject to any disclaimer, the term of this patent is extended or adjusted under 35 U.S.C. 154(b) by 0 days.

(21) Appl. No.: 10/038,565

(22) Filed: Oct. 19, 2001

(65) Prior Publication Data

US 2002/0058013 A1 May 16, 2002

(30) Foreign Application Priority Data

Oct. 20, 2000 (JP) ........................................ 2000-321823

(51) Int. Cl.⁷ ........................... A61K 7/16; A61K 31/70
(52) U.S. Cl. ........................... 424/49; 424/435; 514/29
(58) Field of Search ........................... 424/49–58, 435; 514/29

(56) References Cited

U.S. PATENT DOCUMENTS

| 3,651,208 | A |   | 3/1972  | Lauster ........................ 424/49 |
|-----------|---|---|---------|-------------------------------|
| 5,366,733 | A | * | 11/1994 | Brizzolara et al. .......... 424/426 |
| 5,622,498 | A | * | 4/1997  | Brizzolara et al. ............ 433/80 |
| 5,736,152 | A | * | 4/1998  | Dunn ........................ 424/426 |
| 5,741,782 | A | * | 4/1998  | Brockbank et al. ........... 514/31 |
| 5,880,172 | A | * | 3/1999  | Rajaiah et al. .............. 523/120 |
| 6,069,188 | A | * | 5/2000  | Rajaiah et al. .............. 523/120 |
| 6,080,744 | A | * | 6/2000  | Ayon-Covarrubias ....... 514/252 |
| 6,143,516 | A | * | 11/2000 | Little et al. ................... 435/29 |

FOREIGN PATENT DOCUMENTS

| EP | 0 381 446   | 8/1990 |
| EP | 1 033 127   | 9/2000 |
| WO | WO 94/12150 | 6/1994 |
| WO | WO 95/09601 | 4/1995 |
| WO | WO 98/41224 | 9/1998 |

\* cited by examiner

*Primary Examiner*—Frederick Krass
(74) *Attorney, Agent, or Firm*—Koda & Androlia

(57) ABSTRACT

An oral treatment/care agent including the combination of one or more of an oral bacterial flora-controlling agent that will restore abnormal or sick oral bacteria flora to a normal or healthy oral bacterial state and a periodontal-pocket bacterial flora-controlling agent that will eliminate or convert the bacteria, fungi, viruses and other microbes in a periodontal pocket into a group of symbiotic bacteria. This agent is capable of preventing diseases of the oral tissue and is effective in stopping or slowing the development of a disease in progress.

2 Claims, 2 Drawing Sheets

Amphotericin B

ORAL TREATMENT/CARE AGENT

BACKGROUND OF THE INVENTION

1. Field of the Invention

Figure 1:
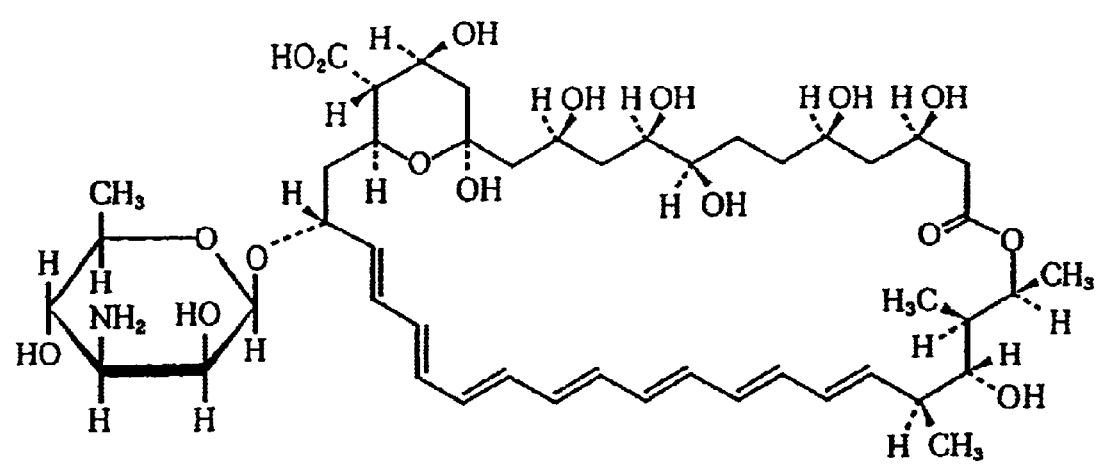

This invention relates to devices and apparatuses to treat and care for oral tissues such as the teeth and periodontium.

2. Prior Art

There have been excisions, exsections and other symptomatic surgical treatments for oral lesions. There have also been medicines for use in symptomatic medicinal treatment incidental to these surgical treatments. While there have been the aforementioned and various other symptomatic treatments, no complete cure or prevention of periodontosis has been possible by the prior art.

SUMMARY OF THE INVENTION

This invention was made in light of the aforementioned circumstances and it is a general object of the invention to provide medicines for the complete cure of periodontosis, to provide treatment medicines for rebuilding the periodontium, and medicines for treating or preventing dental cares.

In keeping with the principles of the present invention, the objects are accomplished by the technical means used in the oral treatment/care agent of this invention as follows:

1. The oral treatment/care agent, such as a dental treatment/care agent or periodontal treatment/care agent, or an intraoral-bone anaplastic agent is characterized by being, at least, an antifungal agent and antibiotic.

2. The oral treatment/care agent, such as a dental treatment/care agent or periodontal treatment/care agent, or an intraoral-bone anaplastic agent is characterized by being, at least, an immunostimulator and antibiotic.

3. The oral treatment/care agent, such as a dental treatment/care agent or periodontal treatment/care agent, or an intraoral-bone anaplastic agent is characterized by containing at least: an oral bacterial flora-controlling agent that will restore abnormal or sick oral bacterial flora to a normal or healthy oral bacterial state; and a periodontal-pocket bacterial flora-controlling agent that will eliminate or convert the bacteria, fungi, viruses and other microbes in a periodontal pocket into a group of symbiotic bacteria.

4. The oral treatment/care agent is further characterized by the inclusion of element N, nitrogen.

5. The oral treatment/care agent is further characterized by the antifungal agent being amphotericin B.

6. The oral treatment/care agent is further characterized by the antibiotic being a macrolide antibiotic.

7. The oral treatment/care agent is characterized by the antibiotic being azithromycin.

8. The oral treatment/care agent is further characterized by having a membrane for rebuilding the periodontium.

9. The oral treatment/care agent is further characterized by having a periodontium inducing agent or dental-pulp inducing agent.

10. The oral treatment/care agent is further characterized by being a component of a prosthesis through application thereto or inclusion therein.

11. The oral treatment/care agent is further characterized by the method of its administration, being any of, or any combination of, mixed, time-release, local or non-local administration.

Since the oral treatment/care agent, such as a dental treatment/care agent or periodontal treatment/care agent, or an intraoral-bone anaplastic agent is characterized by including an antifungal agent and antibiotic, it is chiefly capable of curing periodontosis completely. Still further, since the oral treatment/care agent, such as a dental treatment/care agent or periodontal treatment/care agent, or an intraoral-bone anaplastic agent is characterized by including, at least, an immunostimulator and antibiotic, it is chiefly capable of treating periodontosis effectively.

The oral treatment/care agent of the present invention, such as a dental treatment/care agent or periodontal treatment/care agent, or an intraoral-bone anaplastic agent is characterized by containing at least: an oral bacterial flora-controlling agent that will restore abnormal or sick oral bacterial flora to a normal or healthy oral bacterial state; and a periodontal-pocket bacterial flora-controlling agent that will eliminate or convert the bacteria, fungi, viruses and other microbes in a periodontal pocket into a group of symbiotic bacteria. It is therefore capable of preventing diseases of the oral tissue and is effective in stopping, or slowing the development of, a disease in progress.

Since the oral treatment/care agent is characterized by the inclusion of, at least, element N, nitrogen, it contributes especially to stimulation of the periodontium and helps cure periodontosis.

Since the oral treatment/care agent is further characterized by the antifungal agent being amphotericin B, it is capable of eliminating the fungi that are harmful to a living organism. Since the oral treatment/care agent is especially capable of eliminating *Candida albicans*, it can be used to treat and prevent periodontosis. It is also effective in the treatment and prevention of dental caries. Further, it is capable of preventing and treating the Candida invasion of the oral mucous membrane and periodontium. Also, immunostimulation is expected. The oral treatment/care agent can then be used to maintain the health of the periodontium and other oral tissues, and to treat periodontosis effectively. In particular, the concurrent administration of amphotericin B and azithromycin, especially the commercial product Zithromax, will cure periodontosis completely.

Since the oral treatment/care agent is further characterized by the antibiotic being a macrolide antibiotic, it is capable of completely eliminating, or replacing the bacteria and fungi in a periodontal pocket with minute amounts of cocci or bacilli.

Since the oral treatment/care agent is further characterized by having a membrane for rebuilding the periodontium, it is capable of rebuilding the periodontium effectively.

Since the oral treatment/care agent is further characterized by having a periodontium inducing agent or dental-pulp inducing agent, it is capable of rebuilding the periodontium.

Since the oral treatment/care agent is further characterized by being a component of a prosthesis through application thereto or inclusion therein, it is capable of treating and preventing diseases of the teeth, periodontium or oral mucous membranes that are in contact with the prosthesis.

Since the oral treatment/care agent is characterized by the method of its administration, being any of, or any combination of, mixed, time-release, local or non-local administration, it is capable of providing a medicine efficiently to the lesion in a method appropriate to the case.

BRIEF EXPLANATIONS OF DRAWINGS

Figure 2:
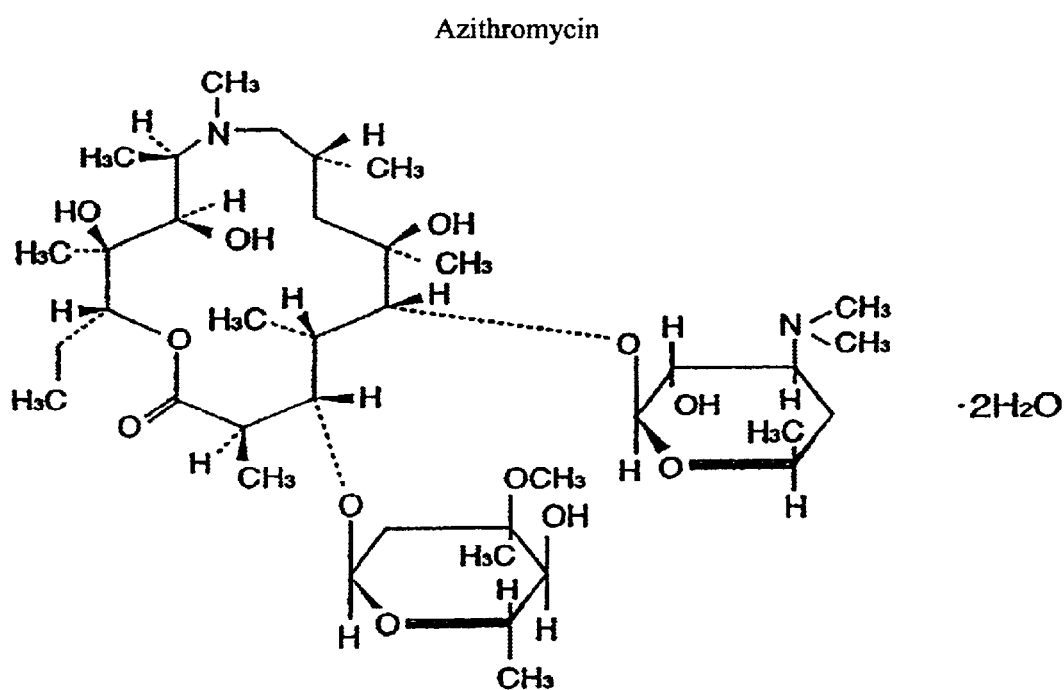

The above-mentioned features and objects of the present invention will become more apparent with reference to the following description taken together with the accompanying drawings wherein like reference numerals denote like elements and in which:

FIG. 1 shows an example of antifungal agent and an example of an immunostimulator; and FIG. 2 shows an example of antibiotic.

DETAILED DESCRIPTION OF THE INVENTION

An explanation for the oral treatment/care agent of this invention follows with reference to the examples or variation thereof for carrying out the invention, as shown in FIGS. 1 and 2. The examples of carrying out the invention are: a medicine whose purpose is to treat or prevent periodontosis; an agent using the medicine for the rebuilding and treatment of the periodontium destroyed or absorbed by periodontosis, or an intraoral-bone anaplastic agent which is an element of the medicine; and the effectiveness of the medicine in treating and preventing dental caries.

First Example

The first example of carrying out the invention shows an agent for the treatment of periodontosis. The same agent may also be used for the prevention of periodontosis. FIGS. 1 and 2 are drawings of examples that explain the oral treatment/care agent.

A medication consisting of amphotericin B of FIG. 1 and azithromycin in FIG. 2 as its components is administered to a living organism. The medicines may or may not be hydrated with $H_2O$ or the like, as in FIG. 2. The medicines may be used alone, or in combination with an aqueous solution, or a carrier listed below, or may be coated with sugar, or mixed with a carrier or additives as used in common medicines.

Specifically, a syrup of amphotericin B is administered inside the mouth and azithromycin is administered orally. Amphotericin of 100 mg/1 mL potency is locally applied to the teeth and periodontium for a period ranging from a day to several months at 0.1 to 1 cc/day, while azithromycin of 500 mg potency/two tablets is administered orally. Another specific example is the local application of 0.1 to 1 cc of the commercial product Halizon syrup over the teeth or periodontium (not into the pocket) together with oral administration of the commercial product called Zithromax for about three days at 500 mg per day via diverse-routed administration or diverse-routed, convergently-acting administration. Here, the term "convergently-acting" means that the medicines act on the same tissue, namely, the periodontium. Strictly speaking, directly or indirectly, Zithromax acts from the deepest portion of or interior of a pocket, while Halizon acts on the upper part of the pocket, the gums and membrane surface, or throughout the mouth as a whole.

If a biofilm or periodontosis bacteria remains in the periodontal pocket one week following the administration of azithromycin, it will be preferable to once again administer azithromycin for three days at 500 mg potency/two tablets. The administration of amphotericin B may be stopped after a period of one week to several months, or re-administered as part of a maintenance program, in consideration of possible hospital or family infection.

Previously, these medicines have not been used against chronic periodontosis, and the use of any single one of the medicines has never cured periodontosis completely. Now, medication using these two medicines, at least, as its chief components has resulted in the complete cure of periodontosis. Here, a complete cure was determined by comparing the configuration and properties (hardness and color, in clinical practice) of the periodontium, mobility of the teeth, depth of pockets, hemorrhaging, pus discharge, effusion, bacterial flora within the pocket and the like, against those of a normal person (excepting any dramatic periodontial regeneration such as dramatic bone growth relative to the normal person through this medication alone).

The speed of the action of this medication on periodontosis was considerable, being on the order of one week for a dramatic change. Even in a severe case it took only about two weeks to stop the hemorrhaging and pus discharge and tighten the gums to a degree equal to that of a normal person, showing the medication's immediate effectiveness. It is also expected that amphotericin B and others, when used in an appropriate frequency in a program of maintenance, would contribute to sustained effectiveness and would thereby offer long-term stability. The use of amphotericin alone has shown annual-term occurrences.

Accordingly, it is very possible that periodontosis, which has heretofore been an incurable disease, is now a curable one. Moreover, these medicines have been found to be an effective, nearly 100-percent in practically every case where the conventional treatment with repeated irrigation, PTC and PMTC has failed to stop pus discharge, hemorrhaging and swelling.

Variation of First Example

The means of "diverse-routed administration" was used in the aforementioned example of carrying out the invention, but any other means may also be utilized. In other words, any means of administration may be freely chosen by the administrator, including: a mixed administration in which the medicines are premixed outside the mouth; a non-local administration in which a medicine is given at a different location; a time-release, non-local administration in which at least the aforementioned two medicines are administered at a time interval, for instance via physical application and oral administration; a time-release administration in which at least two medicines are administered at a time interval; and the diverse administration of injection and physical application. Different means of administration may also be used in combination. An example is an advance administration of azithromycin for three days, followed by the action of amphotericin B. Meanwhile, if amphotericin B is administered in advance, azithromycin may be added when pus discharge or a biofilm is found to persist. These two medicines, with their long-lasting action, feature especially favorable interaction and potentiation with each other, even when they are administered at a long interval.

Another example is that one tablet each of the commercial products Zithromax and Halizon is ground together, and mixed with the carrier shown below, to an approximate five-percent concentration, and then applied to the gum and root canal in a mixed administration. This method is especially suitable for localized administration.

These medicines may also be used in combination with the carriers shown below. One example is to use them mixed with collagen gel. Additionally, the medicines may be used in combination with a bone-inducing factor such as osteoblast or BMP, thus significantly improving the efficiency of bone induction and replacement. Previously the full capability of a bone-anaplastic agent alone, as given through the periodontium, was hampered by infection.

These medicines may also be mixed with about a five-percent glass ionomer or other cement. Such a mixture is well suited for the basing, lyning and capping of a carious cavity. It may also be applied or mixed into the resin portion of a denture. Doing so efficiently disinfects the denture area, which is also an area of Candida growth, with a probable sustained release of the medicines to the tissue. This is an especially efficient method in cases where the denture is in contact with a tooth and dental caries and periodontosis tend to develop easily.

Other Formulation Examples

A1 Formulation: Two-product Mix

Macrolide antibiotic, for example, the commercial product Zithromax, +amphotericin B, for example, the commercial product Halizon.

Effectiveness of the formulation: Action of at least an appropriate amount of the two-product mix on a bacterial group sensitive to the commercial product Zithromax and a fungal group sensitive to amphotericin B, the commercial product Halizon, in the carious cavity and root canal, or a lesion such as a periodontal pocket, is highly effective, exhibiting the inhibited progression of dental caries and a reduction in lesion size at the root apex.

A2 Formulation: Two-product Mix

Macrolide antibiotic, for example, the commercial product Zithromax, +another antifungal.

Effectiveness of the formulation: Action of at least an appropriate amount of the two-product mix on a bacterial group sensitive to the commercial product Zithromax and a fungal group sensitive to an antifungal other than amphotericin B, in the carious cavity and root canal, or a lesion such as a periodontal pocket, is highly effective, exhibiting the inhibited progression of dental caries and a reduction in lesion size at the root apex.

B1 Formulation: Three-product Mix

Macrolide antibiotic, for example, the commercial product Zithromax, +amphotericin B, for example, the commercial product Halizon+metronidazole.

Effectiveness of the formulation: Action of at least an appropriate amount of the three-product mix on a bacterial group sensitive to macrolide antibiotic (for example, the commercial product Zithromax), a fungal group sensitive to amphotericin B, and an anaerobic bacteria group sensitive to metronidazole, in the carious cavity and canal root, or a lesion such as a periodontal pocket, is highly effective, exhibiting the inhibited progression of dental caries and a reduction in lesion size at the root apex.

B2 Formulation: Three-product Mix

Macrolide antibiotic, for example, the commercial product Zithromax, +another antifungal+metronidazole.

Effectiveness of the formulation: Action of at least an appropriate amount of the three-product mix on a bacterial group sensitive to macrolide antibiotic (for example, the commercial product Zithromax), a fungal group sensitive to an antifungal other than amphotericin B, and an anaerobic bacteria group sensitive to metronidazole, in the carious cavity and canal root, or a lesion such as a periodontal pocket, is highly effective, exhibiting the inhibited progression of dental caries and a reduction in lesion size at the root apex.

C1 Formulation: Modified Two-product Mix

Amphotericin B, for example, the commercial product Halizon, +metronidazole, for example, the commercial product Flagyl.

Effectiveness of the formulation: Action of at least an appropriate amount of the modified two-product mix on an anaerobic bacterial group sensitive to metronidazole (for example, the commercial product Flagyl) and a fugal group sensitive to amphotericin B, in the carious cavity and canal root, or a lesion such as a periodontal pocket, is highly effective, exhibiting the inhibited progression of dental caries and a reduction in lesion size at the root apex.

C2 Formulation: Modified Two-product Mix

Another antifungal+metronidazole, for example, the commercial product Flagyl.

Effectiveness of the formulation: Action of at least an appropriate amount of the modified two-product mix on an anaerobic bacterial group sensitive to metronidazole (for example, the commercial product Flagyl) and a fungal group sensitive to an antifungal other than amphotericin B, in the carious cavity and canal root, or a lesion such as a periodontal pocket, is highly effective, exhibiting the inhibited progression of dental caries and a reduction in lesion size at the root apex.

"Another antifungal" is herein defined as miconazole (the commercial product Florid Gel), fluconazole (the commercial product Diflucan), Chinese medicines and the like. This definition is also applicable to "another antifungal" as expressed in other examples.

D1 Formulation

Amphotericin B, for example, the commercial product Halizon, +tetracycline, for example, the commercial product Minomycin.

Effectiveness of the formulation: Action of at least an appropriate amount of the two-product mix on a bacterial group sensitive to tetracycline and a fungal group sensitive to amphotericin B, in the carious cavity and canal root, or a lesion such as a periodontal pocket, is highly effective, exhibiting the inhibited progression of dental caries and a reduction in lesion size at the root apex.

D2 Formulation

Another antifungal+tetracycline, for example, the commercial product Minomycin.

Effectiveness of the formulation: Action of at least an appropriate amount of the two-product mix on a bacterial group sensitive to tetracycline and a fungal group sensitive to an antifungal other than amphotericin B, in the carious cavity and canal root, or a lesion such as a periodontal pocket, is highly effective, exhibiting the inhibited progression of dental caries and a reduction in lesion size at the root apex.

E1 Formulation

Amphotericin B, for example, the commercial product Halizon, +penicillin, for example, the commercial product Yamacillin.

Effectiveness of the formulation: Action of at least an appropriate amount of the two-product mix on a bacterial group sensitive to penicillin and a fungal group sensitive to amphotericin B, in the carious cavity and canal root, or a lesion such as a periodontal pocket, is highly effective, exhibiting the inhibited progression of dental caries and a reduction in lesion size at the root apex.

E2 Formulation

Another antifungal+penicillin, for example, the commercial product Yamacillin.

Effectiveness of the formulation: Action of at least an appropriate amount of the two-product mix on a bacterial group sensitive to penicillin and a fungal group sensitive to an antifungal other than amphotericin B, in the carious cavity and canal root, or a lesion such as a periodontal pocket, is highly effective, exhibiting the inhibited progression of dental caries and a reduction in lesion size at the root apex.

F1 Formulation

Amphotericin B, for example, the commercial product Halizon, +cephem type, for example, the commercial product Kefral.

Effectiveness of the formulation: Action of at least an appropriate amount of the two-product mix on a bacterial group sensitive to the cephem type and a fungal group sensitive to amphotericin B, in the carious cavity and canal root, or a lesion such as a periodontal pocket, is highly effective, exhibiting the inhibited progression of dental caries and a reduction in lesion size at the root apex.

F2 Formulation

Another antifungal+cephem type, for example, the commercial product Kefral.

Effectiveness of the formulation: Action of at least an appropriate amount of the two-product mix on a bacterial group sensitive to the cephem type and a fungal group sensitive to an antifungal other than amphotericin B, in the carious cavity and canal root, or a lesion such as a periodontal pocket, is highly effective, exhibiting the inhibited progression of dental caries and a reduction in lesion size at the root apex.

G Formulation: Four-product Mix

Amphotericin B, for example, the commercial product Halizon or another antifungal+metronidazole, for example, the commercial product Flagyl+cephem type, for example, the commercial product Kefral+ciprofloxacin, for example, the commercial product Ciproxan.

Effectiveness of the formulation: Action of at least an appropriate amount of the four-product mix on a bacterial group sensitive to the cephem type, an anaerobic bacterial group sensitive to metronidazole (for example, the commercial product Flagyl) or ciprofloxacin (for example, the commercial product Ciproxan), and a fungal group sensitive to amphotericin B or another antifungal, in the carious cavity and canal root or a lesion such as a periodontal pocket, is highly effective, exhibiting the inhibited progression of dental caries and a reduction in lesion size at the root apex.

All of the aforementioned formulations are examples of the oral treatment/care agent. Basically, the medicines may be administered after, in advance of, or concurrently with scaling, root-planing, curettage or other surgical treatment to remove the diseased tissue, but administration prior to surgical treatment is recommended whenever possible.

Second Example

The second example of carrying out the invention is a periodontial rebuilding/treatment agent using the medicines in the first example and the first example of variation. Specifically, various kinds of bacteria and fungi have been living inside periodontal pockets, adversely affecting the anaplastic, rebuilding and inducing agents for the periodontium such as the bone-anaplastic and -inducing agents for rebuilding of the periodontium. The effects of the bacteria and fungi have made it difficult or impossible to rebuild the periodontium.

Here, bone anaplastic- and periodontium-inducing agents are added to periodontal pockets where the medicines in the foregoing paragraphs have already been administered. The addition enables one to obtain a level of bone-anaplastic and periodontium-inducing performance that heretofore was unavailable. These are more active periodontium-treating agents than those in the first example of carrying out the invention, and they also serve as intraoral-bone anaplastic agents. Specifically, TCP and apatite-type bone-anaplastic agents are used together with, or following the administration of, the medicines in the first example.

More specifically, the periodontal pocket is filled with the commercial product Emdogain or a tooth germ- or periodontal-ligament-inducing agent using a syringe or the like, one week after the use of the aforementioned medicines. At this point the aforementioned medicines may be administered again. A periodontal pack may also be used concurrently. Moreover, antifungal agents may be applied to, or mixed into, the periodontal pack. The commercial product Zithromax may also be administered for three days at 500 mg per day.

The formulations shown below are suitable for anaplastic work, or for the rebuilding of a deficient area of bone or an area treated for periodontosis.

First Group

Bone-inducing substances such as AMP, osteopontin and osteocalcin.

Second Group

Bone tissues such as—TCP and hydroxyapatite.

Third Group (medicines designated to act on periodontal bacteria and the like):

Antifungal agents, iodine, fluorine, povidone iodine and other antifungal or antibacterial agents, especially, amphotericin B of FIG. 1 and azithromycin of FIG. 2.

Any combination, always including one from the third group, may be used. The combination will suppress the fungi or bacteria attached to the substances from the first or second group, facilitating the rebuilding of periodontal bone.

The method of using a bone-anaplastic material is filling a deficient area of bone, as is the case with conventional ones. Then, any of, or any combination of, the medicines from the third group that has been added to the bone-anaplastic material may be added to the periodontal pocket to enhance the effectiveness of the medicine. The conventional anaplastic material has suffered from the attachment of mostly Candida, but other bacteria as well, thus hindering the affinity between the anaplastic material and the tissue. The use of a third medicine group prevents bacterial deposits, thereby improving the anaplastic material's adhesion to the tissue. The carrier may be poly [(2-oxo-1-pyrrolidinyl) ethylene], dextrin, cyclodextrin, glucan, fibrin, collagen, chondroitin, chitosan, chitin, hyaluronic acid, various amino acids, monoclonal antibody and others. Various membranes for the rebuilding of the periodontium may be used concurrently with the aforementioned medicines. The resultant effectiveness in the rebuilding of the periodontium will exceed that of the use of a membrane exclusively. Bone-inducing agents such as BMP, osteopontin and osteocalcin and (the first group) may be used as a dental-pulp inducing agent. The first and second groups may be used as a periodontal-ligament inducing agent, cement-substrate inducing agent and other periodontium-inducing agent. An example is to use the commercial product Emdogain in place of the first and/or second group.

Example of Composite Variations

The carrier may be poly [(2-oxo-1-pyrrolidinyl) ethylene], dextrin, cyclodextrin, glucan, fibrin, collagen, chondroitin, chitosan, chitin, hyaluronic acid, various amino acids, monoclonal antibody, polyethylene glycol, cellulose, various cements, resins, porcelain, methacrylate, orthophosphate or their derivatives. A carrier may be used in combination with an antifungal agent such as iodine, fluorine or amphotericin B as an antifungal-action medicine. Iodine and fluorine offer another benefit in that they are effective against pathogenic bacteria, and may be used for preventive treatment of the teeth and periodontium or for any other purpose.

The aforementioned medicines may also be used in the specific examples of carriers, as shown below. Examples of medicines are as follows:

1. Glycerin

As explained by this example, concentrated glycerin may be chosen and mixed with fluorine and iodine. The mixture is loaded into a syringe and inserted into a periodontal pocket. Specifically, a few milligrams of iodine are added to one milliliter of glycerin. Fluorine in a minute amount, being on the order of less than a few milligrams per milliliter, may also be added as appropriate. This mixture will remain within the pocket and continuously release the medicine.

2. Poly [(2-oxo-1-pyrrolidinyl) ethylene

Fluorine is mixed with povidone iodine to replace the iodine inclusion and form a compound having an inclusion of fluorine-iodine mixture or fluorine only. Poly [(2-oxo-1-pyrrolidinyl) ethylene] adheres to the inside of a pocket or gum tissue and releases iodine and fluorine continuously. Here, fluorine becomes a preventive agent against fungi and dental caries as it suppresses the Candida enolase, thereby hindering the progression of periodontosis.

3. Gum and tooth powder

Iodine, Chinese natural medicines and various medicinal teas may also be added to gum and tooth powder for the treatment of periodontosis, dental caries and hypersensitivity. Gum is capable of releasing iodine and fluorine in a sustained manner. The paste component in tooth power allows it to attach to the teeth and periodontium, releasing the medicines continuously.

4. Cyclodextrin

Cyclodextrin (CD), especially with fluorine or iodine inclusions, will bind with St. mutans and release the medicine in a sustained manner. When the cyclodextrin inclusion binds with St. mutans that is glucan-connected to Candida, the iodine and fluorine medication can be directed to act with significant efficacy on the Candida.

5. Floss

Iodine and fluorine may be used with conventional liquid floss. The medication may be mechanically inserted into interdental areas and pockets.

In the aforementioned examples fluoride and iodine are used, but the carriers may be those used in the first and second examples of carrying out the invention. The medication may not be limited to fluorine and iodine but may also utilize other halogens or $Ca(OH)_2$. Other medicines such as antifungal agent (amphotericin B) and antibiotic (cephem type, penicillin type, antibacterial agents and the like) may also be used concurrently. A trisaccharide, i.e., 13 glucan, mannan or raffinose may also be administered orally for enhanced immunity against the fungi in living organisms. The aforementioned medicines or antifungal agents may be added to a bone-anaplastic material, which is a form of carrier, to fill a deficient area of bone. The concentration given for the aforementioned medicines is an example. Any concentration over 0 and up to 100 percent may be prepared at any time, depending on the application most suitable for each case. An antifungal agent may be used as an immunostimulator. The means of administration may be left to the discretion of the administrator. It may be topically administered via a toothbrush during brushing, and is a suitable defense against abnormal Candida growth in dental plaque. It may also be used for the prevention of dental caries. It may be applied to a denture or the resin area thereof for the suppression of inflammation or discomfort caused by a denture. Disinfecting efforts may not only target *Candida albicans*, but also at Candida tropicalis, parapsilosis, guilliermondii, krusei, kefyr, glabrata, lusitaniae and others. The aforementioned medicines may be used on Candidiasis other than periodontosis. They may possibly be used for the treatment of cancers.

In other words, since there is a possibility that Candida hampers the activities of the macrophage and white corpuscles, thereby helping to promote cancer, the aforementioned anti-Candida medicines may be able to prevent such an action. There is another possibility that the use of amphotericin B as an anti-Candida medicine may prevent the growth and metastasis of cancer through the immunostimulating action of amphotericin B. The self-propagating Candida gene may possibly be interfering with the human productive gene, causing the runaway proliferation known as cancerization. Yet another possibility may be for a corn cob to carry a carcinogenic virus, bacteria or substance, which upon entry into the tissue may induce cancerization (a natural injection). Since there is the possibility that Candida may be acting as an a HIV carrier to cause HIV infection, the aforementioned medicines may be used for prevention of the infection.

The aforementioned objectives may also be accomplished through the use of a bacterial flora-controlling agent. The mouth must be filled with the bacteria that exist together in symbiotic relationship of an appropriate degree. The growth of various pathogenic bacteria or fungi in such a symbiotic relationship will generate a disease of high risk, a case of dental caries or periodontosis in a person. The restoration of the unbalanced environment to a healthy one is an important objective, and is one of the examples of carrying out the invention. While the mouth must be filled with bacteria existing in a symbiotic relationship of an appropriate degree, the required range of bacterial flora control for a periodontal pocket involves not only the conditions of the cocci and bacilli that are potentially capable of a mutually symbiotic relationship, but also a completely aseptic condition. Needless to say, the bacteria in the mouth as a whole must maintain a symbiotic relationship. The oral bacteria-controlling agent may be an antifungal agent like amphotericin B in FIG. 1, or an oxidizing agent for an anti-mutans. The periodontal-pocket bacteria-controlling agent may be azithromycin in FIG. 2. An immunostimulator may also be used as a controlling agent for the oral bacteria and periodontal-pocket bacteria.

The aforementioned example, or the variation thereof, for carrying out the invention uses azithromycin as the antibiotic. Element C (carbon) in the cyclic structure of this antibiotic was substituted by element N with a resultant change in the electron and proton distributions. A sugar like glucose, fructose or galactose, or an amino acid or lipid, may be used with their elements C and O (oxygen) partially replaced by element N (nitrogen). Any conventional antibiotics and any and all compounds may be used with their elements C and O replaced by element N. The electron and proton distributions will activate periodontal tissue, stimulate white corpuscles and other immunization systems, impart an antibacterial effect, or enhance tissue retention for the compound.

The aforementioned examples, or variation thereof, for carrying out the invention, may be used alone, or in a combination, and may even be used for other purposes. Presently it is felt that the first example of carrying out the invention is the best. The application of an antibiotic into a periodontal pocket should be done while watching closely for the manifestation of a resistant bacteria. The administration of an antifungal agent is also useful in terms of suppressing superinfection resulting directly from an antibiotic. While the concentration and period of administration are left to the administrator's discretion, those shown in the first example of carrying out the invention are recommended. In addition to *Candida albicans*, the fungi that are considered as being closely related to periodontosis include *Candida tropicalis*, parapsilosis, guilliermondii, krusei, kefr, glabrata, lusitaniae and others.

It should be apparent to those skilled in the art that the above-described embodiments and examples are merely illustrative of the examples and embodiments which could be created and utilized in the teachings of the present invention. Numerous and various other arrangements, examples and embodiment can be devised by those skilled in the art without departing from the spirit and scope of the present invention.

We claim:

1. An oral care agent for the treatment of periodontitis, comprising the following components;

(a) an antifungal agent selected from the group consisting of amphotericin B, miconazole and fluconazole;

(b) a macrolide antibiotic; and (c) a component selected from the group consisting of a periodontium rebuilding membrane, a periodontium inducing agent, a dental pulp inducing agent, and a component of a prosthesis;

wherein components (a) and (b) together are more effective for treating periodontitis than either component alone.

2. An oral care agent for the treatment of periodontitis, comprising the following components:

(a) an antifungal agent selected from the group consisting of amphotericin B, miconazole and fluconazole;

(b) azithromycin; and (c) a component selected from the group consisting of a periodontium rebuilding membrane, a periodontium inducing agent, a dental pulp inducing agent, and a component of a prosthesis;

wherein components (a) and (b) together are more effective for treating periodontitis than either component alone.

* * * * *